(12) United States Patent
Sakalosky

(10) Patent No.: US 6,660,762 B2
(45) Date of Patent: Dec. 9, 2003

(54) METHODS AND COMPOSITIONS TO TREAT LUNG DISEASES

(76) Inventor: George P. Sakalosky, 410 Gatlin Dr., Gatlinburg, TN (US) 37738

( * ) Notice: Subject to any disclaimer, the term of this patent is extended or adjusted under 35 U.S.C. 154(b) by 0 days.

(21) Appl. No.: 10/146,607

(22) Filed: May 14, 2002

(65) Prior Publication Data

US 2003/0004204 A1 Jan. 2, 2003

Related U.S. Application Data

(60) Provisional application No. 60/290,751, filed on May 14, 2001.

(51) Int. Cl.[7] ............................................... A61K 31/40
(52) U.S. Cl. ....................................................... 514/410
(58) Field of Search .......................................... 514/410

(56) References Cited

PUBLICATIONS

Mathur, Seema, et al., "Mobilization and Distribution of Beryllium Over the Course of Chelation Therapy with Some Polyamionocarboxylic Acids in the Rat", *Human & Experimental Toxicology* (1993), 12, 19–24.

Sharma, Pragya, et al., "Beryllium–induced Toxicity and its Prevention by Treatment with Chelating Agents", *Journal of Applied Toxicology*, 20, 313–318 (2000).

Occupational Lung Diseases, The Merck Manual of Diagnosis and Therapy—Seventeenth Edition, 1999, Merck Research Laboratories Whitehouse Station p. 619–627.

Berg, S.M., et al., "Pharmaceutical Salts", J. Pharm. Sci., 1997; 66: 1–19.

Norgrady, Thomas, "Medicinal Chemistry A Biomedial Approach", Oxford University Press, New York, (1985), pp. 388–392.

*Primary Examiner*—Kevin E. Weddington
(74) *Attorney, Agent, or Firm*—Dorsey & Whitney LLP; Scott D. Rothenberger

(57) ABSTRACT

Methods, compositions, pharmaceutical compositions and packaged pharmaceuticals that include porphyrin analogues are described. The porphyrin analogues identified in the present application can be used to treat various pneumoconiosic diseases, including berylliosis. Effective treatment by the porphyrin analogues is best accomplished via an aerosol.

20 Claims, 2 Drawing Sheets

```
┌─────────────────────────┐
│  Beryllium added to     │
│  hemoglobin solution    │
│    (2.5 Be: 1 Hb)       │
└─────────────────────────┘
            ↓
┌─────────────────────────┐
│ Incubated at 37°C for 30│
│ minutes. Precipitate    │
│ removed by centrifugation│
└─────────────────────────┘
            ↓
┌──────────────────────────────┐
│ Sample loaded onto 1 x 25 cm │
│ Sephadex G-25 column. Eluted │
│ with HBS. 1 ml eluate        │
│ fractions collected and      │
│ diluted to 5 ml with distilled water │
└──────────────────────────────┘
          ↙       ↘
┌──────────────────────┐  ┌──────────────────────┐
│ Hemoglobin concentration │ Beryllium concentration │
│ determined spectrophotometrically │ determined by ICP │
└──────────────────────┘  └──────────────────────┘
          ↘       ↙
     ┌─────────────────────┐
     │ Ratio of beryllium: │
     │ hemoglobin calculated│
     └─────────────────────┘
```

Figure 1. Method used to determine binding of beryllium to hemoglobin

Figure 1

Figure 2. Effect of porphyrins on beryllium associated with human oxyhemoglobin

METHODS AND COMPOSITIONS TO TREAT LUNG DISEASES

RELATED APPLICATION

This application claims priority to U.S. Provisional Application No. 60/290,751, filed May 14, 2001, entitled "Methods and Compositions to Treat Lung Diseases Associated with Various Metals", the contents of which are incorporated herein by reference in their entirety.

STATEMENT REGARDING FEDERALLY SPONSORED RESEARCH

The U.S. government may have rights in this invention pursuant to U.S. DOE Contract No. DE-FG03-00EH00016.

BACKGROUND OF THE INVENTION

Occupational lung diseases are caused by harmful dust, particles, mists, vapors, or gases inhaled while a person works. The type of lung disease that may develop often depends on where in the airways or lungs an inhaled substance ends up. Many particles can be trapped in the nose or large airways but smaller particles, gases, mists or vapors may reach the lungs. In the lungs, particles may dissolve and may be absorbed into the bloodstream. The solid particles that don't dissolve are generally removed by the body's defenses.

Fortunately, the body has several means to rid inhaled undesired particles. The airways provide mucus that coats particles so they can be coughed up more easily. In particular, the lungs have special scavenger cells that engulf most particles that render the particles harmless to the individual.

The type of particles often produces different reactions in the body. Particles such as plant pollen can cause allergic reactions such as hay fever or asthma. Particles such as coal dust, carbon, and tin oxide don't produce much of a reaction in the lungs but can end up causing serious life threatening results such as black lung disease caused by coal dust. Other particles, such as quartz dust and asbestos, may cause permanent scarring of lung tissue (pulmonary fibrosis). In large enough quantities, certain particles, such as asbestos, can cause cancer in smokers. Lung diseases caused by dusts are called "pneumoconiosis".

Of particular concern is a type of pneumoconiosis, referred to as "berylliosis", and is associated with beryllium. Beryllium is a silver-grey metallic element that occurs in at least 30 minerals and can be found in coal, oil, soil and volcanic dust. Because of its light weight, stiffness, high melting point and high heat capacity, beryllium has been used in various materials such as windshield frames and other structures in high-speed aircraft and space vehicles, aircraft and space shuttle brakes, satellite mirrors and space telescopes, inertial guidance systems and gyroscopes, neutron moderator or reflector in nuclear reactors, X-ray windows and nuclear weapons components.

Beryllium fumes and dust are classified among the most toxic substances currently known. The World Health Organization's International Agency for Research on Cancer, and Agencies of the U.S. Department of Health and Human Service, such as the National Institute for Environmental Health Sciences, and the National Institute for Occupational Safety and Health, have classified beryllium as a possible cause of cancer in humans. The Environmental Protection Agency, by Act of Congress, lists beryllium as a toxic air pollutant that needs to be controlled in our communities. Communities have become contaminated with beryllium from factories, mines or by uncontrolled burning of fossil fuels.

There are two forms of berylliosis: acute and chronic. Acute berylliosis is characterized by a sudden, rapid onset of severe inflammation of the lungs (pneumonitis), coughing, increasing breathlessness (dyspnea), and other associated symptoms. For some individuals, the skin or the eyes may be affected. The more common and chronic form of the disease develops slowly and, in some cases, may not become apparent for many years after initial beryllium exposure. Chronic berylliosis disease (CBD) is characterized by the abnormal formation of inflammatory masses or nodules (granulomas) within certain tissues and organs and widespread scarring and thickening of deep lung tissues (interstitial pulmonary fibrosis). The development of granulomas affects primarily the lungs, however, it may also occur within other bodily tissues and organs, such as the skin and underlying (subcutaneous) tissues or the liver. Individuals with chronic berylliosis are often afflicted with dry coughing, fatigue, weight loss, chest pain, and increasing shortness of breath.

When loss of lung function is detected, treatment may involve taking various corticosteroids, generally referred to as "steroids", medicines that reduce inflammation. One of the most common corticosteroids prescribed for CBD is prednisone. If successful, treatment with prednisone can slow the progress of CBD by reducing the buildup of scar tissue and delaying permanent lung damage. Unfortunately, many individuals do not respond well to steroid treatment. Many individuals cannot tolerate the side effects of long-term steroid treatment, such as slow healing of infections, calcium loss from the bones, higher blood cholesterol, and fluid and salt retention which can cause or aggravate a heart or kidney disease. Individuals who cannot take steroids may continue to lose lung function. As a result they are likely to experience a poorer quality of life, possibly becoming an invalid, and their life span maybe shortened. A need therefore exists, for compositions and methods to prevent lung disease associated with airborne particulates/contaminants that are directed toward the disease process, such that such diseases are physiologically prevented, reversed or inhibited.

SUMMARY OF THE INVENTION

Dusts found in work place environments can affect the body in various ways. Some are not dangerous, others can cause injury and even death. Once inhaled, the components of the dust invade the lungs. Lung diseases caused by dusts are referred to as "pneumoconiosis" and are named by the dust that produces the pneumoconiosis, e.g., beryllium is berylliosis, silica or quartz is silicosis. Surprisingly, it has been discovered that porphyrin analogues, as described below, can remove or prevent build up of these toxic substances in a subject's lung or body tissue(s). Not to be limited by theory, it is considered that the porphyrin analogues have a binding cavity sufficient in diameter with attractive forces (lone pair pi cloud interactions) formed by heteroatoms that complex or chelate with the beryllium metal ion(s). It has been found that non-harmful metal ions already bound by the porphyrin analogue can be displaced by amore toxic metal ion. By porphyrin complexation with these harmful metal ions, the toxic effects of physical contact with these foreign materials can be minimized by the removal of the toxic metals from the tissue(s) by the porphyrin analogues of the present invention.

In one aspect, the present invention provides methods to treat or prevent pneumoconiosis, i.e., berylliosis, in a subject by administering to the subject a therapeutically effective amount of a porphyrin analogue or a pharmaceutically acceptable salt, ester, amide, or prodrug thereof, such that pneumoconiosis in the subject is treated or prevented. A preferred method of administration of the porphyrin analogue or pharmaceutically acceptable salt, ester, amide, or prodrug thereof is in the form of an aerosol. It is considered that administration by use of an inhaler provides a suitable means to bring into contact the porphyrin analogue with the lung tissue most likely affected by the toxic metal(s). Suitable porphyrin analogues include, for example, hemin, meso-tetra (4-carboxyphenyl) porphyrin, phthalocyanine tetrasulfonate, meso-tetra (4-sulfonatophenyl) porphyrin, and magnesium phthalocyanine tetrasulfonate tetra soldium salt porphyrin. In particular, meso-tetra (4-carboxyphenyl) porphyrin and meso-tetra-(4-sulfonate phenyl) have been tested in the lungs of mice and have been found to be non-toxic.

The present invention further provides packaged pharmaceutical compositions for treating or preventing pneumoconiosis in a subject, such as berylliosis. The packaged pharmaceutical compositions include, a container that holds a therapeutically effective amount of at least one porphyrin analogue and pharmaceutically acceptable salts, esters, amides, and prodrugs thereof and instructions for use of the porphyrin analogue for the treatment or prevention of pneumoconiosis in the subject.

The present invention also provides pharmaceutical compositions that include a therapeutically effective amount of at least one porphyrin analogue sufficient to treat or prevent pneumoconiosis, i.e., berylliosis in a subject along with a pharmaceutically acceptable carrier. Preferably the pharmaceutical composition in the carrier can be used in the form of an aerosol for inhalation therapy.

BRIEF DESCRIPTION OF THE DRAWINGS

FIG. 1 is a flow diagram for the determination of beryllium binding by hemoglobin.

DETAILED DESCRIPTION OF THE INVENTION

Figure 2:
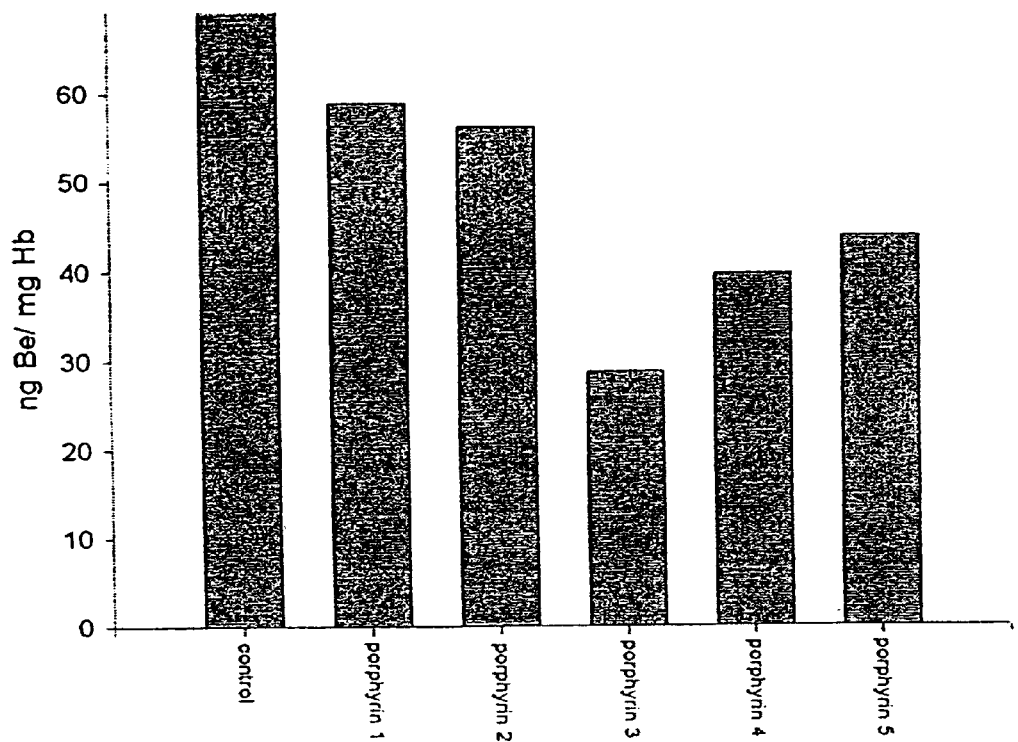
FIG. 2 is a graphical representation demonstrating the removal of beryllium from human oxyhemoglobin by various porphyrin analogues.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

It is to be understood, that throughout the present specification, reference is generally made to porphyrin analogues, as further defined below. However, all pharmaceutically acceptable salts, esters, amides, and prodrugs, including carboxylic acids and their salts, are considered within the scope of the invention. For convenience, this terminology has been minimized throughout the description but should be considered as part of the invention with reference to porphyrin analogues.

The porphyrin analogues of the invention are useful for the treatment of pneumoconiosis (an inflammatory, commonly occupational, disease of the lungs, frequently accompanied by airway obstruction, whether chronic or acute, and occasioned by repeated inhalation of dusts) of whatever type or genesis, including, for example, aluminosis, anthracosis, asbestosis, baritosis, berylliosis, byssinosis, chalicosis, ptilosis, siderosis, silicosis, stannosis, and tabacosis.

The term "porphyrin analogue" as used herein is intended to include macrocyclic heterocycles having an internal cavity capable of complexing or chelating with a metal ion. The porphyrin analogue generally has at least 4 heteroatoms that are interconnected and interrelated via carbon bonds or carbon fragments that further contain additional heteroatoms within the macrocyclic framework. The arrangement of these atoms forms a macrocycle that is considered aromatic. The aromaticity is provided by either an arrangement of unsaturated sites throughout the internal portion of the macrocycle (Formula I) or about the exterior portion of the macrocycle (Formula II) or both, as is generally known in the art. Each A, independently, is a heteroatom, each Z, independently, is a carbon atom or a heteroatom, each Y, independently, is a hydrogen atom, a functional group or when Z is a heteroatom, forms part of a double bond, S and T are each, independently, a functional group or together form a ring and each n is an integer of 1 or 2 to complete the carbon chain.

Formula I

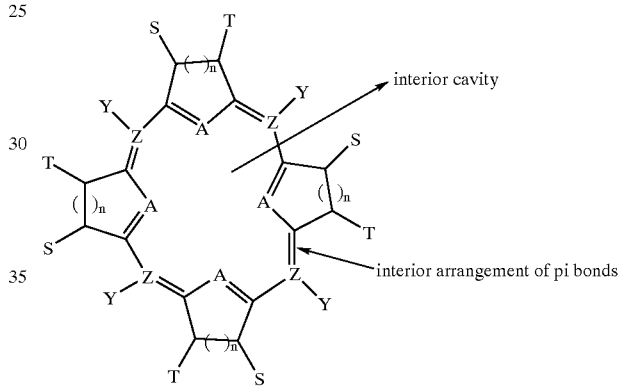

Formula II

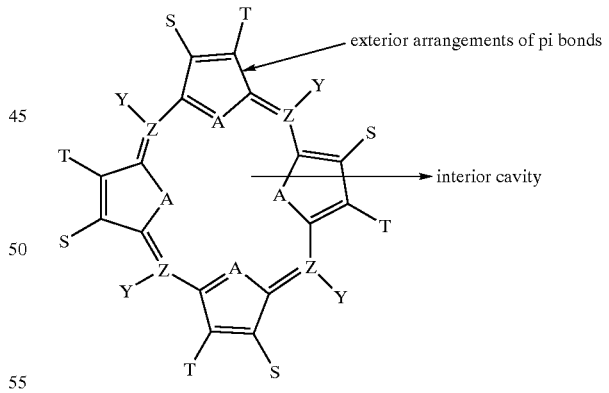

Preferably the heteroatoms A and optionally Z within the macrocyclic structure are each independently chosen from nitrogen, sulfur, oxygen, phosphorous and selenium. In one preferred embodiment, all heteroatoms A (and optionally Z) are nitrogen atoms. In certain embodiments, the macrocycle contains more than one type of heteroatom(s). The arrangement of the heteroatoms provides a framework that forms a cavity located substantially within the middle of the macrocycle. Attractive forces, such as lone pair pi interactions are dimensionally aligned such that metal ions are complexed or chelated within this cavity. By this attraction, undesired metal ions can be removed from a subject's blood or tissues, preferably from lung tissue.

In one aspect of the invention, the porphyrin analogue forms an internal (interior) 16 membered ring as depicted in Formulae I and II. Within the 16-membered ring is an arrangement of at least 4 heteroatoms, preferably nitrogen atoms, wherein the nitrogen atoms located within 5 or 6-membered rings, are spatially separated from one another by 3 atoms. The three atoms can be all carbons or can be two carbon atoms and one heteroatom as defined above. In the instances where heteroatoms Z are part of the 3-atom chain, the porphyrin analogue thus contains a total of 8 heteroatoms. Not all heteroatoms need participate in the coordinate, complexation or chelation of the metal ion.

In certain aspects of the invention, Y is a functional group. The term "functional group" with respect to Y is intended to include substituted and unsubstituted, branched and unbranched alkyl groups, alkylene, and aryl groups.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxy alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylalylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "alkylene" is recognized in the art and is intended to include alkyl groups having one or more degrees of unsaturation. As with the alkyl groups, the alkylene can be branched or unbranched, substituted or unsubstituted and includes those groups described above for the alkyl group.

The term "aryl" as used herein includes 5- and 6-membered single-ring aromatic groups that can include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure can also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. A heteroalkyl moiety is an alkyl substituted with a heteroaromatic group.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, aralkyl, or an aromatic or heteroaromatic moiety.

Preferred functional groups for Y include unsubstituted and substituted phenyl groups, benzyl groups and pyridyl groups. For example, phenols, sulfonated phenyl groups, pyridine and fluorinated alkyl groups, e.g., fluorinated propyl groups are included.

In certain aspects of the invention, S and T, each independently, are functional groups, as described above, hydrogen atoms, or form part of an unsaturated bond within a cyclic structure. Suitable functional groups include methyl, vinyl, alkyl carboxylates, methylol, and lower alkyl groups.

In another embodiment, S and T together form a ring. Suitable cyclic ring structures include those described above for aryl groups. Preferably, when S and T together form a ring, the ring is a six membered ring, forming a phenyl group. Most preferably, the phenyl group is substituted atone or more positions with functional groups described above. In most preferred embodiments, the phenyl group is substituted with a sulfur containing moiety, e.g., a sulfonate. It has been found that sulfur containing moieties attached to the macrocyclic ring of the porphyrin analogue is advantageous for the removal of unwanted metal ions.

Not to be limited by the following, suitable examples of non complexed porphyrin analogues include: Chlorin, Coproporphyrin I Dihyrodrochloride, Coproporphyrin I Tetramethyl Ester, Coproporphyrin III Dihydrochloride, Coproporphyrin III Tetramethyl Ester, Deuteroporphyrin IX 2,4 (4,2), Deuteroporphyrin IX 2-Vinyl 4-Hydroxymethyl, 2,4 Diacetyl Deuteroporphyrin IX Dimethyl Ester, Etioporphyrin I, Hematoporphyrin "D", Hematoporphyrin IX Dimethyl Ester, Hematoporphyrin IX Dihydrochloride, Heptacarboxylporphyrin I Dihyrdrochloride, Heptacarboxylporphyrin I Heptamethyl Ester, Hexacarboxylporphyrin I Dihydrochloride, Hexacarboxylporphyrin I Hexamethyl Ester, Hematoporphyrin IX, Mesoporphyrin IX Dihyrdrochloride, Methyl Mesoporphyrin IX, N-Methyl Protoporphyrin IX, Octaethylporphine, Pentacarboxylporphyrin I Dihydrochloride, Pentacarboxylporphyrin I Pentamethyl Ester, Pentacarboxylporphyrin III Pentamethyl Ester, Pheophorbide a, Phthalocyanine, Phthalocyanine Tetrasulfonate, Porphine, Protoporphyrin IX, Protoporphyrin IX Dimethyl Ester, Protoporphyrin IX Disodium Salt, Purpurin 18, meso-Tetra (4-Carboxyphenyl) Porphine, meso-Tetra (4-Carboxyphenyl) Porphine, meso-Tetra (4-Pyridyl) Porphine, meso-Tetra (4-Sulfonatophenyl) Porphine, meso-Tetra (Heptafluoropropyl) Porphine, meso-Tetra (N-Methyl-4-Pyridyl) Porphine Tetra Tosylate, meso-Tetra (O-Dichlorophenyl) Porphine, meso-Tetra (O-Hydroxyphenyl) Porphine, meso-Tetra (O-Hydroxyphenyl) Porphine, meso-Tetra (Pentafluorophenyl) Porphine, meso-Tetraphenylchlorin, meso-Tetraphenyloctaethylporphine, meso-Tetraphenylporphine, Tetrabenzoporphine, Uroporphyrin I Dihydrochloride, Uroporphyrin I Octamethyl Ester, Uroporphyrin III Octamethyl Dihydrochloride, and Uroporphyrin if Octamethyl Ester. Preparation for these and other porphyrin analogues are known in the art and many are commercially available (See For example, Frontier Scientific, Inc., Box 31, Logan, Utah 84323-0031). Particularly preferred compounds are Bis[5-Pivaloylamido-1,3,4-Thiadiazole-2-Sulfonamidatol] and phthalocyanine tetrasulfonate, which was shown to remove 59% of beryllium from a beryllium-hemoglobin complex (see experimental below).

Not to be limited by the following, suitable examples of complexed porphyrin analogues capable of exchanging the complexed metal for amore toxic metal to be removed from the tissue of a subject include·Al(III) Octaethylporphine, Al(Ei) Phthalocyanine Tetrasulfonate chloride, Co(III) Deuteroporphyrin IX, Co(III) Hematoporphyrin IX, Co(III) Mesoporphyrin IX, Co(III) meso-Tetra (4-Pyridyl) porphine, Co(III) meso-Tetra (4-sulfonatophenyl) porphine, Co(III) Protoporphyrin IX Chloride, Fe(III) Coproporphyrin I, Fe(III) Coproporphyrin III, Fe(III) Deuteroporphyrin IX, Fe(III) Deuteroporphyrin IX Bis Glycol, Fe(III) Deuteroporphyrin Disulfonic Acid, Fe(III) Hematoporphyrin IX, Fe(III) meso-Tetra (4-carboxyphenyl) porphine, Fe(III) meso-Tetra (N-methyl-4-Pyridyl) porphine Tetra Tosylate, Fe(III) meso-Tetra (4-Pyridyl) porphine, Fe(III) meso-Tetra-(4-Sulfonatophenyl) Porphine, Fe(III) Mesoporphyrin IX Chloride (mesohemin), Fe(E) Octaethylporphine, Fe(III) Uroporphyrin I, Mg(II) Coproporphyrin III, Mg(II) Porphine, Mg(II) Protoporphyrin IX Na Salt, Ni(II) Etioporphyrin Ni(II), meso-Tera (4-sulfonatophenyl) porphine, Ni(II) meso-Tetraphenylporphine, Ni(II) Octaethylporphine, TiO Octaethylporphine, TiO meso-Tetra (4-sulfonatophenyl) porphine, Zn(II) Coproporphyrin I, Zn(II) Deuteroporphyrin IX Bis Glycol, Zn(II) Deuteroporphyrin IX Disulfonic Acid, Zn(II) Etioporphyrin I, Zn(II) Hematoporphyrin IX, Zn(II) Hematoporphyrin IX Dimethyl Ester, Zn(II) Iso-hematoporphyrin IX, Zn(II) Mesoporphyrin IX, Zn(II) meso-Tetraphenylporphine, Zn(II) Octaethylporphine, Zn(II) Deuteroporphyrin IX 2,4 Bis Ethylene Glycol, Zn(II) Phthalocyanine Tetrasulfonate, Zn(II) Protoporphyrin IX and Zn(II) Uroporphyrin III. Preparation for these and other porphyrin analogues are known in the art and many are commercially available (See For example, Frontier Scientific, Inc., Box 31, Logan, Utah 84323-0031).

The term "pharmaceutically acceptable salts, esters, amides, and prodrugs" as used herein refers to those salts, amino acid addition salts, esters, amides, and prodrugs of the porphyrin analogues of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in, for example, its free base form with a suitable organic or inorganic acid and isolating the salt thus formed. These can include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977;66:1–19 which is incorporated herein by reference).

The term "prodrug" refers to compounds that are rapidly transformed in vivo to yield prophyrin analogues of Formulae I or II, for example, by hydrolysis in blood. A thorough discussion is provided in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is identified, those of skill in the pharmaceutical art generally can design prodrugs of the compound [see, e.g., Nogrady (1985) Medicinal Chemistry A Biochemical Approach, Oxford University Press, New York, pages 388–392]. Conventional procedures for the selection and preparation of suitable prodrug derivatives are described, for example, in "Design of Prodrugs," ed. H. Bundgaard, Elsevier, 1985. Suitable examples of prodrugs include methyl, ethyl and glycerol esters of corresponding carboxylic acid(s) which can be one of the functional groups of the porphyrin analogue.

The term "ameliorate" is intended to include treatment for, prevention of limiting of and/or inhibition of undesired deposition of metal ions, e.g., beryllium, in a subject's tissue, e.g., lung. The word "treatment" as used above in relation to the treatment of diseases of the airways and lungs, in particular various pneumoconiosis, e.g., berylliosis, is to be understood as embracing both symptomatic and prophylactic modes, that is the immediate treatment, e.g. of acute inflammation (symptomatic treatment) as well as advance treatment to prevent ameliorate or restrict long term symptomology (prophylactic treatment). The term "treatment" as used in the present specification and claims in relation to such diseases is to be interpreted accordingly as including both symptomatic and prophylactic treatment symptomatic treatment to ameliorate acute inflammatory event and prophylactic treatment to restrict on-going inflammatory status and to ameliorate future bronchial exacerbation associated therewith.

The term "subject" as used herein refers to any living organism in which a pneuomoconisoic response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "mammal" as used herein refers to a living organism capable of eliciting response to the inhalation of dust particles. The term subject includes, but is not limited to, humans, nonhuman primates such as chimpanzees and other apes and monkey species, sheep, pigs, goats, horses, dogs, cats, mice, rats and guinea pigs, and the like.

Typically subjects that are afflicted with a pneuomoconisoic disease, including berylliosis, exhibit physical manifestations that include one or more of the following: inflammation of the lungs (pneumonitis), abrupt onsets of coughing, difficulty in breathing, weight loss, fatigue, shortness of breath, chest and joint pain, blood in sputum, rapid heart rate, loss of appetite, fevers and night sweats. In certain disease states, such as berylliosis, abnormal tissue forms in the lungs and lymph nodes can enlarge.

In the past, especially for berylliosis, when loss of lung function was detected, treatment included the use of steroids to reduce inflammation of the lung. Such steroids include albuterol sulfate, beclomethasone, cortisone, dexamethasone, fluticasone propionate, ipratropium bromide, methotrexate, methylprednisolone, prednisolone, prenisone, salmeterol xinafoate and triamcinolone acetonide. However, many subjects do not respond well to steroid treatment. Others cannot tolerate the side effects of long term exposure to steroid treatment. Side effects can include slower healing of infections, calcium loss from bones (osteoporosis), increased levels of blood cholesterol, fluid and salt retention, heart and kidney disease. Advantageously, in contrast to present steroid based treatments, the porphyrin analogues and the methods of the present invention minimize or eliminate the aforementioned drawbacks associated with steroid treatment.

The pharmaceutical compositions of the invention described herein include a "therapeutically effective amount" or a "prophylactically effective amount" of the prophyrin analogues of the invention. A "therapeutically effective amount" refers to an amount effective, at dosages and for periods of time necessary, to achieve the desired therapeutic result, e.g., a diminishment or prevention of inflammation associated with various disease states or conditions, or more preferably a quantifiable removal of toxic metal ions, such as beryllium, from the subject. A therapeutically effective amount of the porphyrin analogue vary according to factors such as the disease state, age, sex, and weight of the individual, and the ability of the porphyrin analogue to elicit a desired response in the individual. A therapeutically effective amount is also one in which any toxic or detrimental effects of the undesired (toxic) metal ion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will generally be less than the therapeutically effective amount.

For example, the prophyrin analogue(s) is administered at a therapeutically effective dosage sufficient to inhibit pneumoconiosic mediated responses, such as, inflammation of the lung, shortness of breath, etc. A "therapeutically effective dosage" preferably reduces the degree of pneuomoconisoic mediated responses in the subject by at least about 20%, more preferably by at least about 40%, even more preferably by at least about 60%, and still more preferably by at least about 80% to 90% relative to untreated subjects. The ability of a compound to inhibit or ameliorate pneuomoconisoic mediated responses can be evaluated in an animal model system that can be predictive of efficacy in treating said responses. Preferably, the pneuomoconisoic mediate response can be monitored by the uptake of the toxic metal ion from the subject. Monitoring can be performed by well known quantitative analytical techniques that can identify specific metal ions.

The present invention provides pharmaceutically acceptable compositions which comprise a therapeutically-effective amount of one or more of the porphyrin analogues described above, formulated together with one or more pharmaceutically acceptable carriers (additives) and/or diluents. As described in detail below, the pharmaceutical compositions of the present invention can be specially formulated for administration in solid or liquid form, including those adapted for the following: oral administration, for example, drenches (aqueous or non-aqueous solutions or suspensions), tablets, boluses, powders, granules, pastes for application to the tongue; parenteral administration, for example, by subcutaneous, intramuscular or intravenous injection as, for example, a sterile solution or suspension; topical application, for example, as a cream, ointment or spray applied to the skin; as an aerosol, or intravaginally or intrarectally, for example, as a pessary, cream or foam.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the porphyrin analogue from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the porphyrin analogue can contain a basic functional group(s) such as, nitrogen(s) and/or amine(s), and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1–19)

In other cases, the porphyrin analogues of the present invention can contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal action, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like.

Formulations of the present invention include those suitable for oral, nasal, topical (including buccal and sublingual), rectal and/or parenteral administration. The formulations can conveniently be presented in unit dosage form and can be prepared by any methods well known in the art of pharmacy. The amount of porphyrin analogue which can be combined with a carrier material to produce a single dosage form will vary depending upon the subject being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as bronchoaveolar lavages for intended delivery systems to the lung and the like, each containing a predetermined amount of a porphyrin analogue of the present invention as an active ingredient. A porphyrin analogue of the present invention can also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar—agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay, lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions of the present invention, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions which can be dissolved in sterile water, or some other sterile injectable medium immediately before use. These compositions can also optionally contain opacifying agents and can be of a composition that they release the active ingredient(s) only, or preferentially in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the porphyrin analogues of the invention include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming and preservative agents.

Suspensions, in addition to the porphyrin analogue, can contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration can be presented as a suppository, which can be prepared by mixing one or more porphyrin analogues of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum and release the active compound.

Formulations of the present invention which are suitable for vaginal administration also include pessaries, creams, gels, pastes, foams or spray formulations containing such carriers as are known in the art to be appropriate.

Dosage forms for the topical or transdermal administration of porphyrin analogues of this invention include powders, sprays, ointments, pastes, creams, lotions, gels, solutions, patches and inhalants. The porphyrin analogue can be mixed under sterile conditions with a pharmaceutically-acceptable carrier, and with any preservatives, buffers, or propellants which can be required.

The ointments, pastes, creams and gels can contain, in addition to a porphyrin analogue of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof Powders and sprays can contain, in addition to a porphyrin analogue of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. In a preferred embodiment, the porphyrin analogue(s) of the invention will be administered topically within the airways, e.g. by the pulmonary route/by inhalation. Advantageously, while having potent efficacy when administered topically, the porphyrin analogues of the invention are devoid of, or exhibit relatively reduced, systemic activity, e.g. following oral administration. The porphyrin analogues of the invention thus provide a means for the treatment of diseases and conditions of the airways or lung, e.g. as hereinabove set forth, with the avoidance of unwanted systemic side effect, e.g. consequent to inadvertent swallowing of drug substance during inhalation therapy.

In general, for treating diseases or conditions of the airways or lungs, e.g. for use in treating inflammatory disease, for example berylliosis, the porphyrin analogue(s) of the invention will suitably be administered topically to the airways or lungs, e.g. by inhalation, at dosages of the order of from 0.01 to 50 mg/day, e.g. from 0.1–5 mg/day, most preferably from 0.4–1.6 mg/day, e.g. administered from a metered delivery system in a series of from 1 to 5 puffs at each administration, with administration performed once to four times daily, e.g., 200–800 $\mu$g once or twice a day by inhalation. Dosages at each administration will thus conveniently be of the order of from about 0.0025 to 10 mg, more suitably from 0.1 to 1.0 mg, e.g. administered with a metered delivery device, e.g. capable of delivering, e.g. 0.02 to 1.0 mg of porphyrin analogue, per administration.

Transdermal patches have the added advantage of providing controlled delivery of a porphyrin analogue of the present invention to the body. Such dosage forms can be made by dissolving or dispersing the porphyrin analogue in the proper medium. Absorption enhancers can also be used to increase the flux of the porphyrin analogue across the skin. The rate of such flux can be controlled by either providing a rate controlling membrane or dispersing the porphyrin analogue in a polymer matrix or gel.

Ophthalmic formulations, eye ointments, powders, solutions and the like, arc also contemplated as being within the scope of this invention.

Pharmaceutical compositions of this invention suitable for parenteral administration comprise one or more porphyrin analogues of the invention in combination with one or more pharmaceutically-acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, solutes which render the formulation isotonic with the blood of the intended recipient or suspending or thickening agents.

Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It is also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In some cases, in order to prolong the effect of a porphyrin analogue, it is desirable to slow the absorption of the porphyrin analogue from subcutaneous or intramuscular injection. This can be accomplished by the use of a liquid suspension of crystalline or amorphous material having poor water solubility. The rate of absorption of the porphyrin analogue then depends upon its rate of dissolution which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the porphyrin analogues of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention can be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a porphyrin analogue or other material other than directly into the central nervous system, such that it enters the patient's system and, thus, is subject to metabolism and other like processes, for example, subcutaneous administration.

Regardless of the route of administration selected, the porphyrin analogues of the present invention, which can be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention can be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a porphyrin analogue of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the porphyrin analogue can be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

EXAMPLES

1. Experimental Design

Quantification of Beryllium Binding to Human Hemoglobin

Beryllium binds to human hemoglobin, but the extent of binding depends on the oxidation state of iron in hemoglobin. Significantly more beryllium bind to oxyhemoglobin and carboxyhemoglobin than methemoglobin. Oxy- and carboxyhemoglobin contain iron in the +II oxidation state, while methemoglobin contains iron in the +III oxidation state.

Quantification of Beryllium Binding to Porphyrins

Nuclear magnetic resonance (NMR) analysis of porphyrin samples with and without beryllium suggested that beryllium reacted with porphyrins. Mass spectrometric (MS) analysis was not found to confirm the reaction suggested by NMR. Furthermore, MS analysis indicated some discrepancy between stated molecular weights of porphyrins.

Determination of the Ability of Porphyrins to Chelate Beryllium Bound to Hemoglobin Incubation of beryllium bound to hemoglobin and porphyrins (hemin (porphyrin 1), meso-tetra (4-carboxyphenyl) porphyrin (porphyrin 2), phthalocyanine tetrasulfonate (porphyrin 3), meso-tetra (4-sulfonatophenyl) porphyrin (porphyrin 4), or magnesium phthalocyanine tetrasulfonate tetra sodium salt porphyrin (porphyrin 5)) reduced the amount of beryllium associated with hemoglobin, indicating that the porphyrin test compounds can indeed chelate beryllium from hemoglobin. The results were most striking for porphyrin 3.

2. Binding of Beryllium to Hemoglobin

2.1 Methods

These experiments used beryllium nitrate (Aldrich 46,503–8) as a soluble form of beryllium. When added to phosphate buffered saline (PBS), pH 7.4, a precipitate formed that did not dissolve at 37° C. This precipitate was probably an insoluble beryllium phosphate complex. Due to the insolubility of beryllium in PBS at necessary concentrations, experiments were carried out in N-2hydroxyethylpiperazine-N'-2-ethane-sulfonic acid (HEPES)-buffered saline (HBS). HEPES is commonly used as a buffer for biochemical experiments in the physiological pH range. HBS contained 10 mM HEPES, sodium chloride, and potassium chloride, pH 7.4.

Human hemoglobin (Sigma H7379) was dissolved in HBS at a concentration of 40 mg/ml. This hemoglobin was >95% methemoglobin. To reduce the iron and form oxyhemoglobin, 5 mM sodium hydrosulfite was added to the hemoglobin solution. This solution was then dialyzed overnight at 4° C. against HBS to remove residual sodium hydrosulfite. To form carboxyhemoglobin, oxyhemoglobin was gently bubbled with carbon monoxide for 5 minutes. Identity of hemoglobins was confirmed by spectrophotometry prior to experimentation.

Beryllium nitrate was added to a solution of hemoglobin at a molar ratio of 2.5:1 (B e: Hb). This mixture was incubated at 37° C. for 30 minutes. During incubation with beryllium some precipitation of hemoglobin occurred. Precipitate was removed from the samples by centrifugation. Samples of hemoglobin with no beryllium were used as negative controls. Experiments were performed on oxy-, met-, and carboxyhemoglobin.

To isolate beryllium bound to hemoglobin (Be—Hb) from free beryllium, samples were passed through a 1 cm×25 cm Sephadex G-25 column equilibrated in HBS. One milliliter fractions of column eluate were collected. These fractions were diluted to 5 ml with distilled water. The hemoglobin content of each fraction was determined by use of Drabkin's reagent. Beryllium content of each fraction was determined by inductively coupled plasma atomic absorption spectrophotometry (ICP-AAS). A flow chart of this procedure is presented as FIG. 1.

2.2 Results

Beryllium binds to human hemoglobin. The amount of beryllium bound to hemoglobin is dependent on the oxidation state of iron in the heme. Significantly more beryllium bound to oxyhemoglobin and carboxyhemoglobin than methemoglobin (see Table 1 below). Both oxy- and carboxyhemoglobin contain iron in the +II oxidation state, while methemoglobin contains iron in the +III oxidation state. The dependence on oxidation state suggests a reaction involving the heme moiety of hemoglobin, but no changes in the UV spectra of any hemoglobin after incubation with beryllium were observed.

TABLE 1

Binding of beryllium to various hemoglobins following incubation at 37° C. for 30 minutes.

| Type of hemoglobin | µg beryllium/ mg hemoglobin Mean Std. Deviation | | Molar ratio (moles Be:moles Hb) Mean Std. Deviation | |
|---|---|---|---|---|
| Methemoglobin | 0.016[a] | 0.004 | 0.13a | 0.10 |
| Oxyhemoglobin | 0.438 | 0.085 | 2.25 | 0.22 |
| Carboxyhemoglobin | 0.351 | 0.148 | 1.88 | 0.35 |

[a] denotes values that are significantly different from oxyhemoglobin ($P < 0.05$).

3. Binding OP Beryllium to Porphyrins

3.1 Nuclear Magnetic Resonance (NMR)

Initial experiments utilized HBS prepared in deuterium oxide (deuterated water, $D_2O$) to eliminate the protons of water. This was not successful as the HEPES in the buffer also contains protons that interfered with the analysis. Therefore, experiments were conducted with porphyrins 1–5 dissolved in deuterium oxide. Porphyrins were analyzed in the presence and absence of beryllium-Spectra were collected on a 500 MHz JEOL.

The addition of beryllium to solutions of porphyrin 3 and 5 produced shifts and a change in the signal (in the aromatic region) in the proton NMR spectra that suggest a reaction of beryllium with the porphyrin.

3.2 Mass Spectrometry (MS)

As with NMR experiments, use of a buffer suppressed ionization of the porphyrins and prevented accurate analysis of the sample. MS experiments were conducted in distilled water. Samples were submitted to Washington University Resource for Biomedical and Bio-organic Mass Spectrometry in St. Louis, Mo. Samples were analyzed on a Finnigan LCQ mass spectrometer using electrospray ionization. The instrument was run in the negative ion mode using acetonitrile:methanol:water (1:1:1) as the solvent. Porphyrin 3 was mixed with beryllium and 2,6-lutidine at room temperature and at 60° C. to synthesize a beryllium complex.

MS analysis of the potential beryllium-porphyrin complexes was performed. No change in the mass spectra indicative of formation of the beryllium porphyrin complex was observed, even upon heating to 60° C. in the presence of lutidine. While the observed mass of porphyrin 1 matched the theoretical formula, the observed masses of porphyrins 2 through 5 did not.

4. Chelation of Hemoglobin Bound Beryllium by Porphyrins

4.1 Methods

Beryllium bound to oxyhemoglobin (Be—Hb) was prepared as described in Section 2.1 (above). To determine if the test porphyrins were able to remove beryllium from hemoglobin, porphyrins were added to the hemoglobin solution at 2.5 times the Be concentration of the solution. One hundred μl of 7.1 mM porphyrin solution (or 100 μl of HBS for controls) was added to 1 ml of Be—. This mixture was incubated at 37° C. for 30 minutes. Following incubation, the entire mixture was loaded into a Centricon YM-30 molecular weight cutoff filter. This filter retains molecules with a molecular weight >30,000 (i.e., hemoglobin) and allows smaller molecules (i.e. porphyrin, free beryllium) to pass through. The samples were centrifuged to concentrate hemoglobin on the filter and then washed with 500 μl of HBS to remove any porphyrin or beryllium trapped in the hemoglobin concentrate. Hemoglobin concentrates were collected in 100 μl of HBS according to the manufacturer's instructions. The concentrates were then diluted to 3 mls with HBS. Hemoglobin concentration of each sample was determined spectrophotometrically with Drabkin's reagent. Beryllium content of each sample was determined by ICP-AAS.

4.2 Results

When a pre-formed beryllium-hemoglobin complex was incubated with a molar excess of porphyrins for 30 minutes at 37° C., the amount of beryllium associated with hemoglobin was reduced (FIG. 2). The most striking reduction occurred with porphyrin 3, which reduced the amount of beryllium associated with hemoglobin by 59%.

5.0 Toxicity

Competitive binding experiments were conducted that established that interaction of beryllium with hemoglobin (Hb) can replace the heme iron and be chelated by Hb and interaction of five different candidate porphyrin compounds with the Be—Hb complex would remove the beryllium from the Be—Hb complex. Chelation of beryllium by Hb and subsequently from Hb by the porphyrin compounds did occur. The three porphyrins studied were phthalocyanine tetrasulfonate porphyrin, meso-tetra (4-carboxyphenyl) porphyrin, meso-tetra (4-sulfonatophenyl) porphyrin.

Toxicity of the three porphyrins were studied. Porphyrins were delivered via aerosols into mice. It is considered that beryllium-lung burdened mice will provide in vivo data for the removal of beryllium via urinary secretion tests.

Aqueous solutions of the three porphyrins were aerosolized using a constant-flow Pulmo-Mist pump and nebulizer syste and delivered into cages each housing five female 20+ week old C3H/HEJ mice over a period of twenty days. The group bodyweights of these mice were measured each morning prior to aerosol treatment. Regimens included multiple, constant dosing and dose escalation. Mice in cages receiving multiple doses of 9 mg of one of the select porphyrins began to lose weight (up to 14%) by the third day of treatment. When treatment was suspended after day 5 to allow bodyweight normalization, and then resumed on day 14, the weight loss was delayed compared to the first sequence, suggestive of some tolerance induction. Tolerance was also observed with the dose-escalation study, in that treatment with 18 mg on day 6 resulted in about a 21% weight loss on day 15; whereas following weight normalization, treatment with 27 mg on day 20 only resulted in about 12% weight loss. Treatments with two porphyrins generally reflected lower and delayed evidence of toxicity compared to that observed with one of the select porphyrins (phthalocyanine tetrasulfonate porphyrin, meso-tetra (4-carboxyphenyl) porphyrin, meso-tetra (4-sulfonatophenyl) porphyrin). Younger mice (about 6 weeks old) were generally more tolerant than older mice, but the rank order of porphyrin toxicity was the same. The results suggest that beryllium binding porphyrins (phthalocyanine tetrasulfonate porphyrin, meso-tetra (4-carboxyphenyl) porphyrin, meso-tetra (4-sulfonatophenyl) porphyrin) maybe safely delivered as aerosols to C3H/HEJ mice, to allow evaluation of reduction of a beryllium load in the lungs of mice as an intervention in the development of chronic beryllium disease.

6. Discussion

The extent of beryllium binding to hemoglobin under a given set of conditions was quantified. However, the strength of this bond was not determined. The beryllium-hemoglobin complex was strong enough to withstand separation on a Sephadex size exclusion column, indicating that the beryllium is indeed bound to hemoglobin and not trapped in the matrix of the protein.

Binding of beryllium to each of the porphyrins was not quantified. There were minor changes in the ultraviolet or visible spectra of the porphyrins upon addition of beryllium, but were not used to quantify binding. NMR spectra of porphyrins exhibited shifts upon addition of beryllium that suggested an interaction. MS was not able to confirm the interaction of beryllium with porphyrins. Binding of beryllium to porphyrins would be observed as a change of +9 in the apparent mass of fragments in the mass spectrum of the porphyrin upon addition of beryllium. Because the NMR and MS experiments had to be performed in the absence of a buffer, it is possible that pH changes in the solution prevented or slowed the interaction of beryllium and hemoglobin which do occur at pH 7.4.

Those skilled in the art will know, or be able to ascertain, using no more than routine experimentation, many equivalents to the specific embodiments of the invention described herein. These and all other equivalents are intended to be encompassed by the following claims. All publications and references cited herein, including those in the background section, are expressly incorporated herein by reference in their entirety.

What is claimed is:

1. A method to treat a subject having berylliosis comprising the step of administering to the subject a therapeutically effective amount of a porphyrin analogue or a pharmaceutically acceptable salt, ester, amide, or prodrug thereof.

2. The method of claim 1, wherein the porphyrin analogue or pharmaceutically acceptable salt, ester, amide, or prodrug thereof is administered as an aerosol.

3. The method of claim 2, wherein the aerosol is administered in conjunction with an inhaler.

4. The method of claim 1, wherein the porphyrin analogue is hemin, meso-tetra (4-carboxyphenyl) porphyrin, phthalocyanine tetrasulfonate, meso-tetra (4-sulfonatophenyl) porphyrin, or magnesium phthalocyanine tetrasulfonate tetra sodium salt porphyrin.

5. The method of claim 1, wherein the porphyrin analogue comprises at least 4 interconnected heteroatoms in an organic structure that provides a binding site for a metal ion associated with pneumoconiosis.

6. The method of claim 5, wherein the heteroatoms are each independently nitrogen, oxygen, sulfur, or selenium and combinations thereof.

7. The method of claim 6, wherein each of the four heteroatoms are nitrogen atoms.

8. The method of claim 6, wherein at least two of the four heteroatoms are nitrogen atoms.

9. The method of claim 6, wherein the porphyrin analogue has at least one functional group appended thereto.

10. The method of claim 9, wherein the functional group comprises a sulfur moiety.

11. The method of claim 10, wherein the sulfur moiety is a sulfonate.

12. The method of claim 9, wherein the functional group comprises a carboxylate.

13. The method of claim 12, wherein the porphyrin analogue chelates the metal ion associated with pneumoconiosis.

14. The method of claim 13, wherein the metal ion is an element, a metal oxide, a mineral or a metal salt.

15. The method of claim 5, wherein the porphyrin analogue has the following formula (Formula I):

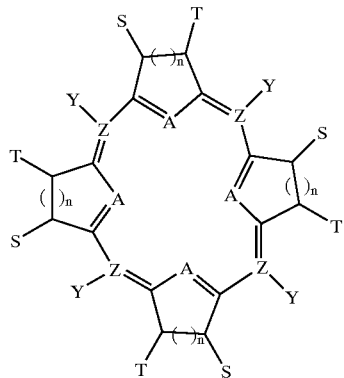

Formula I wherein each A, independently, is a heteroatom;
each Z, independently, is a carbon atom or a heteroatom;
each Y, independently, is a hydrogen atom, a functional group or when Z is a heteroatom, forms part of a double bond;
S and T are each, independently, a functional group or together form a ring; and
each n is an integer of 1 or 2 to complete the carbon chain.

16. The method of claim 15, wherein each A is a nitrogen atom, each Z is a nitrogen atom or a carbon atom, S and T together form a pyrrole or a phenyl group, and n=1, wherein the pyrrole or phenyl group is substituted with at least one sulfur containing moiety.

17. The method of claim 16, wherein the sulfur containing moiety is a sulfonate.

18. The method of claim 5, wherein the porphyrin analogue has the following formula (Formula II):

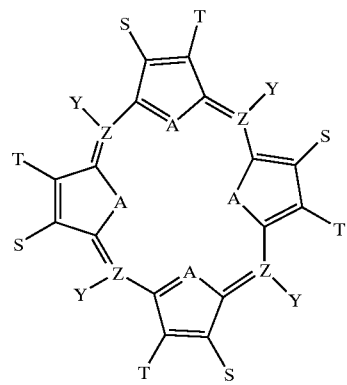

Formula II wherein each A, independently, is a heteroatom;
each Z, independently, is a carbon atom or a heteroatom;
each Y, independently, is a hydrogen atom, a functional group or when Z is a heteroatom, forms part of a double bond; and
S and T are each, independently, a functional group or together form a ring.

19. The method of claim 18, wherein each A is a nitrogen atom, each Z is a nitrogen atom or a carbon atom, S and T together form a pyrrole or a phenyl group, and wherein the pyrrole or phenyl group is substituted with at least one sulfur containing moiety.

20. The method of claim 19, wherein the sulfur containing moiety is a sulfonate.

* * * * *

UNITED STATES PATENT AND TRADEMARK OFFICE
CERTIFICATE OF CORRECTION

PATENT NO. : 6,660,762 B2
DATED : December 9, 2003
INVENTOR(S) : George P. Sakalosky It is certified that error appears in the above-identified patent and that said Letters Patent is hereby corrected as shown below:

Column 2,
Line 61, "amore" should read -- a more -- therefor.

Column 7,
Line 12, "atone" should read -- at one -- therefor.
Line 62, "amore" should read -- a more -- therefor.

Column 8,
Line 9, "Fe(E)" should read -- Fe(III) -- therefor.

Column 13,
Line 53, "thereof Besides inert" should read -- therefor. and Besides inert should be a new paragraph -- therefor.

Column 17,
Line 56, "(B e: Hb)" should read -- (Be:Hb) -- therefor.

Column 20,
Line 4, "maybe" should read -- may be -- therefor.

Signed and Sealed this

Sixth Day of April, 2004

JON W. DUDAS
*Acting Director of the United States Patent and Trademark Office*